(12) United States Patent
Gu

(10) Patent No.: US 10,114,008 B2
(45) Date of Patent: Oct. 30, 2018

(54) METHODS AND DEVICES FOR HIGH THROUGHPUT SCREENING OF CONDITIONS AFFECTING STEM CELL DIFFERENTIATION

(71) Applicant: Empire Technology Development LLC, Wilmington, DE (US)

(72) Inventor: Yansong Gu, Bellevue, WA (US)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 163 days.

(21) Appl. No.: 15/112,660

(22) PCT Filed: Jan. 21, 2014

(86) PCT No.: PCT/US2014/012335
§ 371 (c)(1),
(2) Date: Jul. 19, 2016

(87) PCT Pub. No.: WO2015/112120
PCT Pub. Date: Jul. 30, 2015

(65) Prior Publication Data
US 2016/0334390 A1    Nov. 17, 2016

(51) Int. Cl.
*G01N 33/50* (2006.01)

(52) U.S. Cl.
CPC ..... *G01N 33/5029* (2013.01); *G01N 33/5005* (2013.01); *G01N 33/5008* (2013.01); *G01N 33/5073* (2013.01)

(58) Field of Classification Search
CPC .......... G01N 33/5029; G01N 33/5005; G01N 33/5008; G01N 33/5073
See application file for complete search history.

(56) References Cited

U.S. PATENT DOCUMENTS

| | | | |
|---|---|---|---|
| 4,822,470 A | 4/1989 | Chang | |
| 6,673,606 B1 * | 1/2004 | Tennekoon | C12N 5/0622 424/93.1 |
| 7,339,671 B2 | 3/2008 | Peng | |
| 7,563,825 B1 | 7/2009 | Kahn | |
| 7,572,623 B2 | 8/2009 | Mangano et al. | |
| 7,867,369 B2 | 1/2011 | Bhullar et al. | |

(Continued)

FOREIGN PATENT DOCUMENTS

| | | |
|---|---|---|
| CN | 1865932 A | 11/2006 |
| EP | 1412724 B1 | 3/2016 |

(Continued)

OTHER PUBLICATIONS

Audet, J., et al., "Advances in hematopoietic stem cell culture," Current Opinion in Biotechnology, vol. 9, Issue 2, pp. 146-151 (Apr. 1998).

(Continued)

*Primary Examiner* — Allison M Fox

(57) ABSTRACT

Disclosed are methods and systems for testing the effects of various morphogens and/or feeder cells on the differentiation of pluripotent cells. The assays described herein can be used for determining the optimum conditions that lead to differentiation of stem cells. Once the optimum conditions for stem cell differentiation are determined, such cells may be used in a variety of therapies.

44 Claims, 6 Drawing Sheets

(56) References Cited

U.S. PATENT DOCUMENTS

| | | | |
|---|---|---|---|
| 8,169,610 | B2 | 5/2012 | Oldham et al. |
| 9,701,941 | B2 * | 7/2017 | Danielyan ............ C12N 5/0622 |
| 2003/0113812 | A1 | 6/2003 | Hemperly |
| 2009/0017834 | A1 | 1/2009 | Lim et al. |
| 2009/0017836 | A1 | 1/2009 | Lee |
| 2009/0019632 | A1 | 1/2009 | Mineo |
| 2009/0170198 | A1 | 7/2009 | Rezania |
| 2009/0175836 | A1 | 7/2009 | Brodsky |
| 2009/0191631 | A1 | 7/2009 | Bornemann |
| 2009/0202498 | A1 | 8/2009 | Davidson et al. |
| 2009/0246869 | A1 | 10/2009 | Tseng et al. |
| 2009/0311703 | A1 | 12/2009 | D'Amour et al. |
| 2012/0099323 | A1 | 4/2012 | Thompson |
| 2012/0190108 | A1 | 7/2012 | Poole |
| 2012/0202261 | A1 | 8/2012 | Gu |
| 2013/0302396 | A1 | 11/2013 | Mooney et al. |

FOREIGN PATENT DOCUMENTS

| | | | |
|---|---|---|---|
| WO | 2009048675 | A1 | 4/2009 |
| WO | 2009138512 | A1 | 11/2009 |
| WO | 2011090792 | A1 | 7/2011 |

OTHER PUBLICATIONS

Berardi, A.C., et al., "Functional Isolation and Characterization Human Hematopoietic Stem Cells," Science, vol. 1, 267, No. 5194, pp. 104-108 (Jan. 6, 1995).

Guillaume, D.J., and Zhang, S-C., "Human embryonic stem cells: a potential source of transplantable neural progenitor cells," Neurosurg Focus, vol. 24, Issue 3-4, E3, pp. 1-7 (Mar.-Apr. 2008).

Hu, B-Y., et al., "Neural differentiation of human induced pluripotent stem cells follows developmental principles but with variable potency," Proceedings of the National Academy of Sciences of the United States of America, vol. 107, No. 9, pp. 4335-4340 (Mar. 2, 2010).

International Search Report and Written Opinion for International Application No. PCT/US2014/012335, dated Apr. 1, 2014.

Kobel, S., and Lutolf, M.P., "High-throughput methods to define complex stem cell niches," Biotechniques, vol. 48, No. 4, pp. IX-XXII (Apr. 2010).

Korin, N., and Levenberg, S., "Engineering Human Embryonic Stem Cell Differentiation," Biotechnology and Genetic Engineering Reviews, vol. 24, 243-262 (2007).

Skottman, H., and Hovatta, O., "Culture conditions for human embryonic stem cells," Reproduction, vol. 132, No. 5, pp. 691-698 (Nov. 1, 2006).

"AMOLED," Wikipedia, accessed at https://web.archive.org/web/20130816162303/http://en.wikipedia.org/wiki/AMOLED, last modified on Jul. 29, 2013, pp. 8.

"Dot pitch," Wikipedia, accessed at https://web.archive.org/web/20130827143249/http://en.wikipedia.org/wiki/Pixel_pitch, last modified on Aug. 6, 2013, pp. 4.

"Graphic LCDS & OLEDS," accessed at https://www.crystalfontz.com/c/graphic-lcds-&-oleds/17?cat_id=17, accessed on Feb. 3, 2016, pp. 210.

"OLED," Wikipedia, accessed at https://web.archive.org/web/20130825215958/http://en.wikipedia.org/wiki/Organic_light-emitting_diode, last modified on Aug. 24, 2013, pp. 21.

"Thin-film transistor," Wikipedia, accessed at http://web.archive.org/web/20130617110323/http://en.wikipedia.org/wiki/Thin-film_transistor, last modified on Jun. 13, 2013, pp. 3.

Brivanlou, A.H., et al., "Stem cells. Setting standards for human embryonic stem cells," Science, vol. 300, Issue 5621, pp. 913-916 (May 9, 2003).

Extended European Search Report for European Application No. 13892965.8 dated Mar. 7, 2017, pp. 11.

Hepp, A., et al., "Light-Emitting Field-Effect Transistor Based on a Tetracene Thin Film," Physical Review Letters, vol. 91, Issue 15, pp. 157406-1-157406-4 (Oct. 10, 2003).

International Search Report and Written Opinion for International Application No. PCT/US2013/058244 dated Feb. 6, 2014, pp. 8.

Liu, Y-J., et al., "A micropillar-integrated smart microfluidic device for specific capture and sorting of cells," Electrophoresis, vol. 28, Issue 24, pp. 4713-4722 (Dec. 2007).

Parrish, K., "DuPont Creates 50" OLED in Under 2 Minutes," Tom's Guide, accessed at http://web.archive.org/web/20130514070846/http://www.tomsguide.com/us/OLED-Printing-Display-dupont-HDTV,news-6818.html, May 17, 2010, pp. 4.

Wallace, J., "MicroOLED unveils highest-pixel-density OLED microdisplay," accessed at http://www.laserfocusworld.com/articles/2012/01/microoled-unveils-highest-pixel-density-oled-microdisplay.html, Jan. 30, 2012, pp. 2.

* cited by examiner

METHODS AND DEVICES FOR HIGH THROUGHPUT SCREENING OF CONDITIONS AFFECTING STEM CELL DIFFERENTIATION

CROSS-REFERENCE TO RELATED APPLICATION

This application is a U.S. National Stage Application under 35 U.S.C. § 371 of International Application No. PCT/US2014/012335, filed on Jan. 21, 2014, the entire contents of which are hereby incorporated by reference in their entirety.

TECHNICAL FIELD

The present technology relates generally to the field of cell biology. More specifically, it relates to the propagation and differentiation of pluripotent stem cells, and culture conditions and materials that facilitate differentiation and use of stem cells.

BACKGROUND

The following description is provided to assist the understanding of the reader. None of the information provided or references cited is admitted to be prior art.

Stem cells are cells having the ability to self-renew and divide to an unlimited extent and to differentiate under suitable circumstances to form different types of cells. Embryonic stem cells (ES cells) are stem cells established from early embryos which can be cultured over a long period of time while maintaining pluripotent ability to differentiate into all kinds of cells existing in living bodies. By contrast, somatic stem cells are any cell which is found in a developed organism that has the ability to divide and create another cell like itself and also divide and create a cell more differentiated than itself.

Induced pluripotent stem (iPS) cells are reprogrammed from somatic cells that are capable of differentiating into almost all lineages of cells. For example, it is known that skin fibroblasts may be reprogrammed into iPS. Stem cell treatments using iPS cells hold promises for treating many types of illness, such as degenerative diseases and cancer. However, reprogramming somatic cells usually results in multiple iPS clones and individual iPS clones may differ from each other, for example, in pluripotency due to different telomere lengths in individual somatic cells. Currently, assays to determine pluripotency of iPS cells requires an injection of iPS cells into Scid mice and waiting several months until the mice develop a teratoma (Brivanlou et al. (2003). *Science* 300, 913-916).

The field of regenerative medicine encompasses therapies designed to aid the repair, replacement, or regeneration of damaged cells, tissues, or organs. Stem cell-based therapies have the promise of treating a variety of health conditions including Alzheimer's disease, Parkinson's disease, stroke, spinal injuries, heart attack, renal failure, osteoporosis, type I diabetes, multiple sclerosis, rheumatoid arthritis, burns, and wounds. However, the progress of such therapies has been hindered by a range of factors, including the possibility of immune rejection of ES cells derived from a donor who is immunologically incompatible with the recipient. Furthermore, different lineages of stem cells are needed for treating different conditions.

SUMMARY

The present technology provides methods and cell culture systems for identifying a pluripotency profile of stem cells.

In one aspect, the present technology provides methods for identifying a pluripotency profile of stem cells including: culturing one or more stem cells in a cell culturing system, wherein the cell culturing system comprises a cell culturing plate comprising a layer of cell culturing substrate, a cell culture site comprising the one or more stem cells, and one or more morphogen sites comprising one or more morphogens, wherein the one or more morphogen sites are each positioned peripheral to the cell culture site; incubating the cell culturing system under conditions suitable to allow the one or more stem cells to differentiate into one or more differentiated cells and migrate on the cell culturing plate in response to the one or more morphogens; and determining the migration pattern of the one or more differentiated cells on the cell culturing plate, wherein the migration pattern of the one or more differentiated cells is indicative of the pluripotency profile of the population of stem cells.

In another aspect the present technology provides methods for identifying a stem cell morphogen including: culturing one or more stem cells in a cell culturing system, wherein the cell culturing system comprises a cell culturing plate comprising a layer of cell culturing substrate, a cell culture site comprising the one or more stem cells, and one or more morphogen sites comprising one or more test agents, wherein the one or more morphogen sites are each positioned peripheral to the cell culture site; incubating the cell culturing system under conditions suitable to allow the one or more stem cells to differentiate into one or more differentiated cells and migrate on the cell culturing plate in response to the one or more test agents; and determining the migration pattern of the one or more differentiated cells on the cell culturing plate, wherein the migration pattern of the one or more differentiated cells is indicative of test agent's efficacy as a morphogen.

In some embodiments, the method further includes isolating the one or more differentiated cells that have migrated towards the one or more morphogen sites. In some embodiments, the migration of a desired differentiated cell on the cell culturing plate towards the one or more morphogen sites is indicative of a target morphogen condition to induce differentiation. In some embodiments, the migration of the one or more differentiated cells towards a test agent is indicative of a stem cell morphogen. In some embodiments, the one or more morphogen sites include different concentrations of the same morphogen. In some embodiments, each of the one or more morphogen sites includes a different morphogen.

In some embodiments of the foregoing aspect, each of the one or more morphogen sites are separated by physical barriers in the cell culturing plate. In some embodiments, the cell culture site is surrounded by a physical barrier. In some embodiments, the physical barrier is removed from around the cell culture site.

In some embodiments, each of the one or more morphogen sites are an equal distance away from the cell culture site. In some embodiments, each of the one or more morphogen sites physically overlaps one another.

In some embodiments, each of the one or more morphogen sites includes a chemokine or growth factor. In some embodiments, the chemokine or growth factor includes a molecule selected from the group consisting of: decapentaplegic (Dpp), transforming growth factor beta (TGF-β), hedgehog, sonic hedgehog, wingless/wnt, epidermal growth factor, fibroblastic growth factor, insulin-like growth factor, retinoic acid, and mixtures thereof.

In some embodiments, the cell culturing substrate includes an ingredient selected from the group consisting of gelatin, agarose and agar. In some embodiments, the cell culturing substrate is solid or semi-solid.

In some embodiments, the cell culturing plate is physically divided into one or more compartments.

In yet another aspect, the present technology provides methods for identifying a pluripotency profile of stem cells including: culturing one or more stem cells in a cell culturing system, wherein the cell culturing system comprises a cell culturing plate comprising a layer of cell culturing substrate, a cell culture site comprising the one or more stem cells, and one or more morphogen sites comprising one or more feeder cells, wherein the one or more morphogen sites are each positioned peripheral to the cell culture site; incubating the cell culturing system under conditions suitable for the feeder cells to produce one or more morphogens, and to allow the one or more stem cells to differentiate into one or more differentiated cells and migrate on the cell culturing plate; and determining the migration pattern of the one or more differentiated cells on the cell culturing plate, wherein the migration pattern of the one or more differentiated cells is indicative of the pluripotency profile of the population of stem cells.

In still another aspect, the present technology provides methods for identifying a feeder a cell population for stem cell differentiation including: culturing one or more stem cells in a cell culturing system, wherein the cell culturing system comprises a cell culturing plate comprising a layer of cell culturing substrate, a cell culture site comprising the one or more stem cells, and one or more morphogen sites comprising one or more test feeder cells, wherein the one or more morphogen sites are each positioned peripheral to the cell culture site; incubating the cell culturing system under conditions suitable for the feeder cells to produce one or more morphogens, and to allow the one or more stem cells to differentiate into one or more differentiated cells and migrate on the cell culturing plate; and determining the migration pattern of the one or more differentiated cells on the cell culturing plate, wherein the migration pattern of the one or more differentiated cells is indicative of test feeder cell's efficacy on stem cell differentiation.

In some embodiments, the method further includes isolating the one or more differentiated cells that have migrated towards the one or more morphogen sites. In some embodiments, the migration of a desired differentiated cell on the cell culturing plate towards the one or more morphogen sites is indicative of a feeder cell population for desirable stem cell differentiation. In some embodiments, the migration of the one or more differentiated cells towards the one or more feeder cells in the morphogen site is indicative of a feeder cell type useful to induce differentiation of the stem cell. In some embodiments, the one or more feeder cells comprise a heterogeneous population of feeder cells or a homogenous population of feeder cells. In some embodiments, each of the one or more morphogen sites is separated by physical barriers in the cell culturing plate.

In some embodiments, the cell culture site is surrounded by a physical barrier. In some embodiments the physical barrier is removed from around the cell culture site.

In some embodiments, each of the one or more morphogen sites are an equal distance away from the cell culture site. In some embodiments, each of the one or more morphogen sites physically overlaps one another.

In some embodiments, the one or more feeder cells secrete a chemokine or growth factor. In some embodiments, the chemokine or growth factor comprises a molecule selected from the group consisting of: decapentaplegic (Dpp), transforming growth factor beta (TGF-β), hedgehog, sonic hedgehog, wingless/wnt, epidermal growth factor, fibroblastic growth factor, insulin-like growth factor, retinoic acid, and mixtures thereof.

In some embodiments, the cell culturing substrate comprises an ingredient selected from the group consisting of gelatin, agarose and agar. In some embodiments, the cell culturing substrate is solid or semi-solid.

In some embodiments, the cell culturing plate is visually or physically divided into one or more compartments.

In yet another aspect, the present technology provides a cell culturing system including a cell culturing plate, wherein the cell culturing plate includes a layer of cell culturing substrate; a cell culture site comprising one or more stem cells; and one or more morphogen sites, wherein the one or more morphogen sites are each positioned peripheral to the cell culture site.

In some embodiments, the one or more morphogen sites include different concentrations of the same morphogen. In some embodiments, each of the one or more test spots comprises a different morphogen. In some embodiments, the one or more morphogen sites comprise one or more feeder cells. In some embodiments, the one or more morphogen sites comprise a heterogeneous population of feeder cells or a homogenous population of feeder cells.

In some embodiments, the cell culture site is surrounded by a physical barrier. In some embodiments, the physical barrier is removed from around the cell culture site. In some embodiments, each of the one or more morphogen sites is separated by physical barriers in the cell culturing plate. In some embodiments, the cell culturing plate is visually or physically divided into one or more compartments.

In some embodiments, each of the one or more morphogen sites are an equal distance away from the cell culture site. In some embodiments, each of the one or more morphogen sites physically overlaps one another.

In some embodiments, each of the one or more morphogen sites comprises a chemokine or growth factor. In some embodiments, the chemokine or growth factor comprises a molecule selected from the group consisting of: decapentaplegic (Dpp), transforming growth factor beta (TGF-β), hedgehog, sonic hedgehog, wingless/wnt, epidermal growth factor, fibroblastic growth factor, insulin-like growth factor, retinoic acid, and mixtures thereof.

In some embodiments, the cell culturing substrate comprises an ingredient selected from the group consisting of gelatin, agarose and agar. In some embodiments, the cell culturing substrate is solid or semi-solid.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

Figure 1:
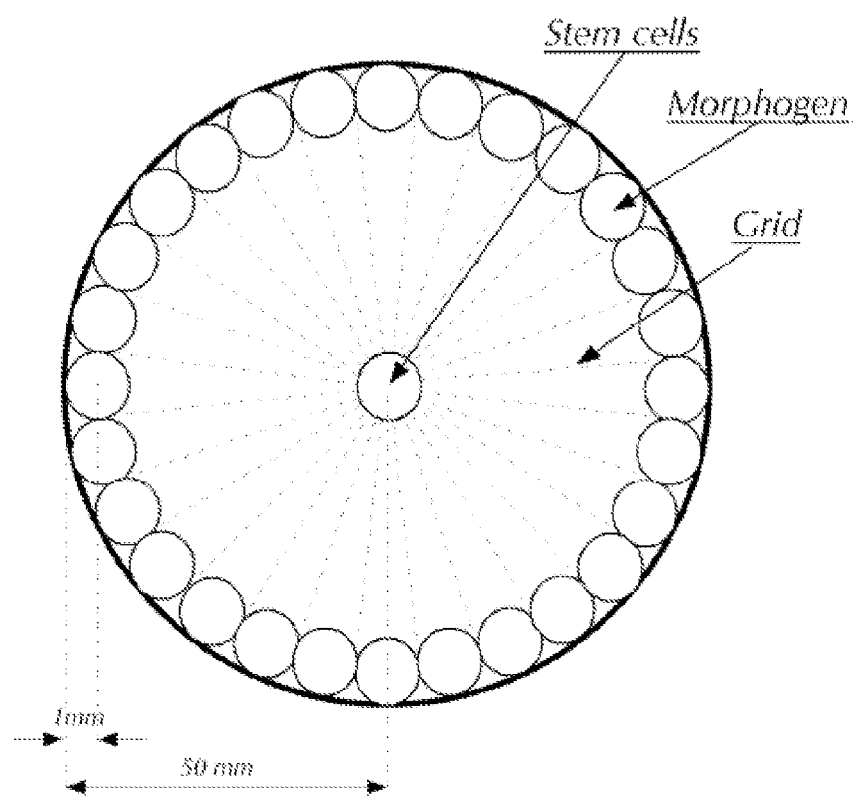
FIG. 1 is an illustrative embodiment showing one arrangement of morphogens and stem cells on a Petri plate.

In the following detailed description, reference may be made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented here.

As used herein, unless otherwise stated, the singular forms "a," "an," and "the" include plural reference. Thus, for example, a reference to "a cell" includes a plurality of cells.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

As used herein, the term "concentration gradient" refers to a gradually increasing concentration of an agent, wherein the location of highest agent concentration is at the agent source.

As used herein, the term "feeder cells" refers to cells of one type that are co-cultured with cells of another type, to provide an environment in which the cells of the second type can grow. In some embodiments, stem cells are co-cultured with feeder cells in order to induce differentiation and chemotaxis of the stem cells.

As used herein, the term "isolated" means that materials naturally accompanying a substance in normal circumstances are at least reduced, or substantially or completely eliminated. In some embodiments, an isolated material constitutes at least about 50%, at least about 75%, at least about 80%, at least about 85%, at least about 90%, at least about 95%, or at least about 99% by weight of a sample containing it. The term "isolated cell" refers to a cell substantially free from other accompanying substances present in natural circumstances (e.g., other cells, proteins, nucleic acids, etc.). The term "isolated" in relation to nucleic acids or polypeptides means that, for example, the nucleic acids or the polypeptides are substantially free from cellular substances or culture media when they are produced by recombinant DNA techniques; or precursory chemical substances or other chemical substances when they are chemically synthesized.

As used herein, the term "morphogen" refers to a molecule or mixture of molecules that induces differentiation, chemotaxis, and/or proliferation of a PS cell. In one embodiment, the morphogen provides spatial information via a concentration gradient that can affect patterning of a differentiating PS cell culture. In some embodiments, a morphogen is a diffusible protein, cytokine, or growth factor.

As used herein the term "pluripotent stem cells" (PS cells) are cells that are capable under the right conditions of producing progeny of several different cell types. PS cells are capable of producing progeny that are derivatives of each of the three germ layers: endoderm, mesoderm, and ectoderm, according to a standard art-accepted test, such as the ability to form a teratoma in a suitable host, or the ability to differentiate into cells stainable for markers representing tissue types of all three germ layers in culture. Included in the definition of PS cells are embryonic cells of various types, such as embryonic stem (ES) cells, as well as induced pluripotent stem cells (iPS) that have been reprogrammed from an adult somatic cell.

Those skilled in the art will appreciate that except where explicitly required otherwise, PS cells includes primary tissue and established lines that bear phenotypic characteristics of PS cells, and derivatives of such lines that still have the capacity of producing progeny of each of the three germ layers. PS cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated PS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated PS cells, and may contain at least 40%, 60%, or 80% undifferentiated PS cells.

As used herein, the term "induced pluripotent stem cells" (abbreviated "iPS cells") refers to cells having properties similar to those of ES cells and encompasses undifferentiated cells artificially derived from a non-pluripotent cell, typically an adult somatic cell.

As used herein, the term "somatic cell" refers to any cell other than germ cells, such as but not limited to an egg, a sperm, or the like, which does not directly transfer its DNA to the next generation. Typically, somatic cells have limited or no pluripotency. Somatic cells used herein may be naturally-occurring or genetically-modified.

As used herein, the term "cell culturing substrate" refers to a substrate that facilitates cell survival and growth. Cell culturing substrate may aid in attachment of cells to the substrate. The substrate may be made of purified proteins or protein mixtures from a cell line, plant cells, or algae, and may be solid or semi-solid. The substrate may be a hydrogel or other synthetic substrate that may be mixed with proteins, sugars, cytokines, or other molecules that may aid in cell survival and growth. Non-limiting exemplary cell culturing matrices include: proteins secreted by Engelbreth-Holm-Swarm Mouse Tumor cells sold under the trademarks Matrigel™ and Geltrex® LDEV-Free Matrix Products; a defined substrate containing components of human origin sold under the trademark CellStart™ CTS™; an alginate-based matrix sold under the trademark AlgiMatrix™; a mixture of recombinant human cell adhesion proteins sold under the trademark StemXVivo™ Culture Matrix; a hydrogel peptide scaffold sold under the trademark PuraMatrix™; collagen; laminin; fibronectin; vitronectin; gelatin; and agar.

As used herein, the term "cell culture site" refers to a defined area in a cell culture system where stem cells are cultured and then tested for their response to a morphogen. For example, a cell culture site may be a well created in a layer of cell culturing substrate into which the stem cells are placed and then cultured.

As used herein, the term "morphogen site" refers to a defined area in a cell culture system where morphogens are placed when testing stem cells or morphogens using the present technology. A morphogen site may contain a purified morphogen or a mixture of morphogens. A morphogen site may also contain one or more feeder cells that express one or more morphogens in culture. An exemplary morphogen site may be a well created in a layer of cell culturing substrate into which morphogen or feeder cells are placed.

As used herein, the term paracrine signaling area refers to a gradient of morphogen that has diffused away from a morphogen site.

As used herein, the term "pluripotency profile" refers to a description of the physical location of differentiated cells from a population of stem cells (putative or known) when cultured using the present technology and exposed to a set of morphogens. For example, a population of stem cells known to be pluripotent and simultaneously exposed to morphogens using the present technology will show a migration pattern of, for example, mesoderm, endoderm, and ectoderm cells towards the morphogen site(s) that induce such differentiation. In another example, a cell population that is only able to produce mesoderm cells will show a different migration pattern when exposed to the same morphogens placed at the same locations.

Devices and Methods for Screening Differentiating Stem Cells with Morphogens

Morphogens are molecules governing, for example, the pattern of cell proliferation and tissue development and the positions of various specialized cell types within a tissue. During development, morphogens guide and control the differentiation of stem cells into a desired lineage of cells.

In one aspect, the present disclosure provides systems and devices for identifying morphogens that guide cell proliferation, differentiation and/or chemotaxis of PS cells. Without wishing to be limited by theory, it is known that the differentiation of stem cells to progenitor cells during embryonic development involves actions of various morphogens coupled with chemotaxis. The morphogen spreads from a localized source and forms a concentration gradient across a developing tissue. In the presence of a chemical gradient, cells may chemotax, or direct their overall motion based on the gradient. Chemotaxis is prevalent in the early phases of embryogenesis as the development of germ layers is guided by gradients of signal molecules.

During early development, morphogen gradients generate different cell types in distinct spatial order. In other words, the morphogen provides spatial information by forming a concentration gradient that subdivides a field of cells by inducing or maintaining the expression of different target genes at distinct concentration thresholds. Thus, for example, cells far from the source of the morphogen will receive low levels of morphogen and express low threshold target genes. For example, cells close to the source of morphogen will receive high levels of morphogen and may express both low and high threshold target genes, or only high level genes. Distinct cell types emerge as a consequence of the different combinations of target gene expression. In this way, the field of cells is subdivided into different types according to their position relative to the source of the morphogen. This is a general mechanism by which cell type diversity can be generated in animal development.

In one aspect, the present disclosure provides devices and methods that may be used to screen morphogens that affect the pluripotency of PS cells. The methods may be used to screen a wide variety of compounds and culture conditions to determine their effect on the differentiation of stem cells. For instance, the methods may be performed with one or more putative differentiation-inducing compounds including, but not limited to, growth factors, cytokines, factors involved in cell-to-cell interactions, adhesion molecules, extracellular matrix components, media components, environmental conditions, etc. The present methods also include screening to identify previously unknown substances that induce proliferation, differentiation and/or chemotaxis.

In one illustrative embodiment, the device includes a culturing plate having a layer of cell culture media, wherein the cell culture media includes a central cell culture site and a plurality of morphogen sites surrounding the central cell culture site, wherein the morphogen sites are separated from each other, and each morphogen site is an equal distance away from the central spot, and wherein each morphogen site is in fluid communication with the central spot. The morphogen site on the culturing substrate may be an equal distance away from each other with no physical divider between each other. Alternatively, the morphogen sites may be separated from each other with a physical barrier. The cell culture sites and morphogen sites may be any shape, e.g., round or oval, or polygonal (e.g. rectangular).

In one illustrative embodiment, PS cells loaded at the center culturing spot come from the same clone. Any desirable numbers of morphogens, including both control morphogens, such as IGF, and chemicals to be tested for morphogenicity, are loaded at the morphogen sites.

In some embodiments, the morphogenic effect of the test chemicals may be assessed based on the location of differentiated cell colonies relative to the central spot and compared to the control morphogen. By way of example, but not by limitation, two identical differentiated cell colonies at similar relative positions to control and test morphogen sites in the paracrine signaling area would indicate that a tested morphogen(s) have the same or similar morphogenic effect as the control morphogen.

In some embodiments, the present technology is used to analyze the effect of the combination of one or more morphogens. By way of example, but not by limitation, the combination of one or more morphogens seeded surrounding the center spot may cause the target cell in the center spot to have a distinct directional migration as compared to the control. The movement of the target cell could be interpreted as an attraction to the combination or an aversion to the combination on the opposite side.

In an illustrative embodiment, the device is a round Petri dish with grids for identifying the placement of morphogens at various locations on the plate. The Petri dish is coated with a layer of cell culture media. As a non-limiting example, the layer may be a semi-solid layer of gelatin, agarose, or agar, among others. The cell culture site of PS cells is located at the center of the plate. In some embodiments, at least one PS cell is seeded in the center. In some embodiments, between about 1 to about 100, or between about 100 to about 250, or between about 250 to about 500, or between about 500 to about 750, or between about 750 to about 1000 PS cells are seeded in the center. In some embodiments, a single embroid body of about 1000 PS cells is seeded in the center. In some embodiments, the morphogen sites are located at the edge of the plate surrounding the central spot. In some embodiments, the position of each of the morphogen sites can be identified according to the grids scored to the bottom of the Petri dish. (FIG. 1)

In some embodiments, cells are seeded in the center of the device. In the case of an individual clone of PS cells, a physical barrier, such as a round tube, may be used to temporarily isolate the media having PS cells from the surrounding media allowing the PS cells to grow in the absence of any test morphogen(s). When the colony has grown to a sufficient size to study the effects of the morphogen(s) on the differentiation and/or chemotaxis of the cells, the physical barrier may be removed allowing the PS cells to have contact the surrounding media that includes the morphogen. In some embodiments, a sufficient size colony is about 1000 cells, or about 1500 cell, or about 2000 cells. Alternatively, or additionally, in some embodiments, the diameter of a sufficient size colony is about 50 µM, or about 75 µM, or about 100 µM, or about 150 µM, or ranges between any of these values. Alternatively, or additionally, in some embodiments, the distance between a sufficient sized colony and the morphogens is about 1 mm to about 1000 mm, or about 10 mm to about 900 mm, or about 50 mm to about 800 mm, or about 100 mm to about 700 mm, or about 200 mm to about 600 mm, or about 300 mm to about 500 mm, or ranges between any of these values.

In one embodiment, the layer of culturing substrate may be a layer of agar. In some embodiments, the PS cells are cultured in Matrigel medium. The PS cells are cultured on the central culturing spot and the surrounding morphogen sites may each contain a morphogen or a morphogen mixture. The morphogen or morphogen mixtures in the morphogen sites may be different from each other in chemical identity, chemical composition, or concentration.

Figure 3:
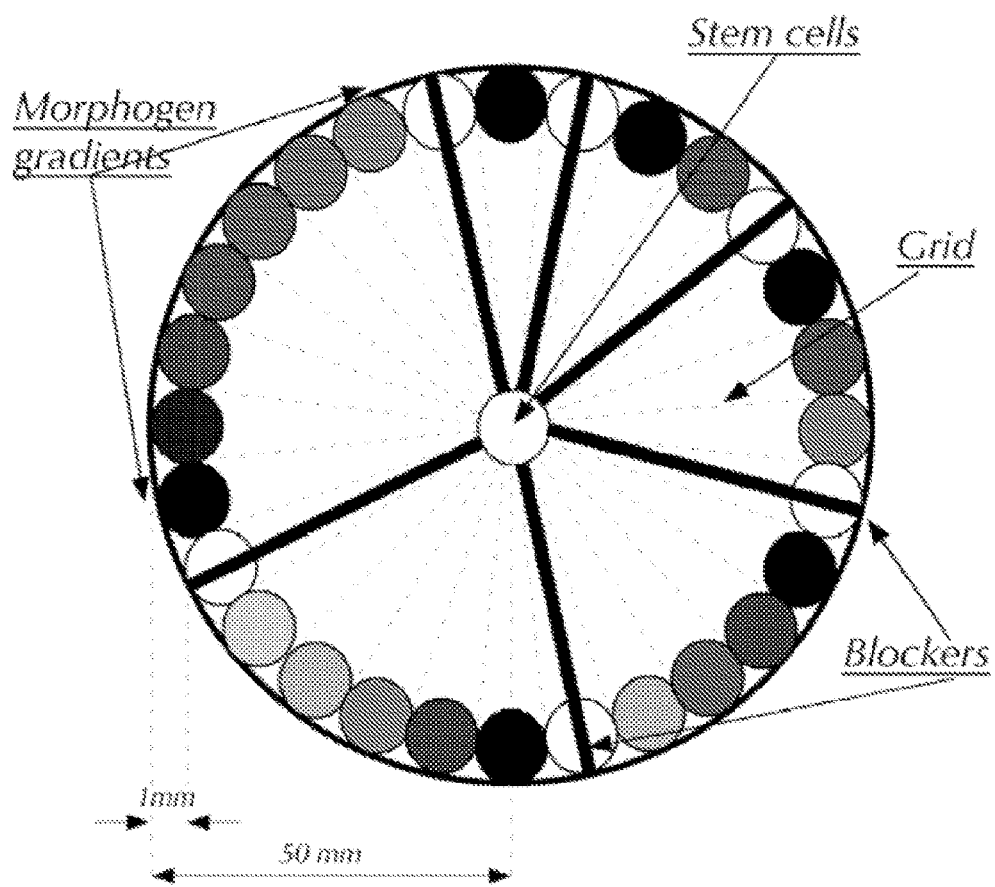
FIG. 3 is an illustrative embodiment showing one arrangement of morphogens and stem cells on a Petri dish containing blocking walls between selected sections to control the diffusion of the morphogens.

In an illustrative embodiment, the Petri dish may have physical dividers between the morphogen sites to provide a plurality of morphogen blocks, as shown in FIG. 3. In this configuration, the PS cells are exposed to only one or a limited number of morphogens in each block. Alternatively, the Petri dish may have no physical dividers between the morphogen sites, as shown in FIG. 1. In this configuration, the PS cells are exposed to a mix of morphogens in the overlapped area.

In another embodiment, the plate may have a 3D structure similar to that disclosed in U.S. Patent Application No. 20090191631. Briefly, the 3D culture dish has an interior culture space with two or more independent hollow fiber capillary membrane systems, each exhibiting a multitude of hollow fiber membranes. The ends of the hollow fiber capillary membrane systems are bundled at each end, with one bundled end to act as a joint inlet, and the other bundled end to act as a joint outlet. Fluids/media and/or gas are passed through the hollow fiber capillary membrane systems via the joint inlet and joint outlet. The capillary hollow fiber membranes are arranged in an alternating pattern in the culture space, whereas the hollow fiber membranes of at least one a pair of hollow fiber membrane systems are—at least in sections—arranged in parallel to each other in one plane. In some embodiments, the detection of cell differentiation or cell migration includes, but is not limited to, examination of the culture dish under microscope or fixing and staining of the culture dish followed by microscope analysis.

Figure 2:
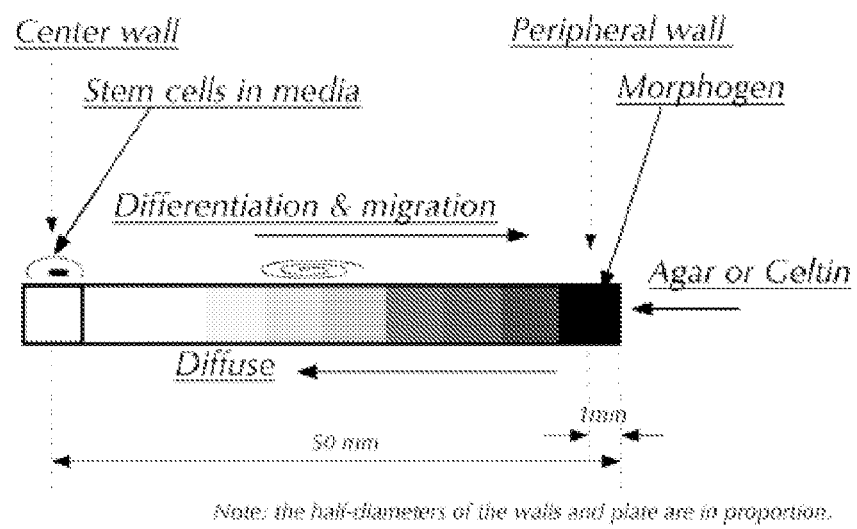
FIG. 2 is a schematic diagram showing the diffusion of morphogens relative to stem cells in an illustrative embodiment.

In another aspect, the methods and assays of the present disclosure may be used to screen the pluripotency of a putative PS colony. When a putative PS colony is cultured, e.g., at a central cell culture site, a differentiated cell tends to migrate toward and propagate at an agar location having an optimal mix of morphogen for this specific differentiated cell (FIG. 1 and FIG. 2). By fixing the time and content of PS cell culture conditions, the distribution of differentiated cells from this PS cell colony typically constitutes a stable pattern, which reflects the pluripotency profile of the tested PS cell. For example, a population of stem cells known to be pluripotent and simultaneously exposed to morphogens using the present technology will show a migration pattern of mesoderm, endoderm, and ectoderm cells towards the morphogen site(s) that induce such differentiation. In another example, a cell population that is only able to produce mesoderm cells will show a different migration pattern when exposed to the same morphogens placed at the same locations. The present technology may be used to test uncharacterized cell populations that may produce differentiated cells from one or more of the germ layers under the proper morphogen conditions.

The present technology may also be used to determine a target morphogen condition required to differentiate a stem cell population. In an illustrative embodiment, several morphogens that may or may not cause differentiation in an uncharacterized stem cell population are placed in separate morphogen sites surrounding a central cell culturing site. In some embodiments, the approximate concentration of morphogen where the differentiated cells are located, and/or the ratio of multiple morphogens with overlapping paracrine signaling areas may indicate a target morphogen condition for differentiating the stem cells or putative stem cells being tested.

In addition to determining a pluripotency profile of stem cells, the present technology can be used to isolate one or more differentiated cells that have migrated towards one or more morphogen spots. In an illustrative embodiment, after observing differentiated cells that have migrated towards a given morphogen site, the differentiated cell or cells may be isolated and cultured for further analysis and study.

Pluripotent Cells

The screening assays described herein may be performed with any appropriate pluripotent cells, or cells derived therefrom. Such cells may include inner cell mass (ICM) cells, embryonic stem (ES) cells, embryonic germ (EG) cells, embryos consisting of one or more cells, embryoid body (embryoid) cells, morula-derived cells, as well as multipotent partially differentiated embryonic stem cells taken from later in the embryonic development process, and also adult stem cells, including but not limited to nestin positive neural stem cells, mesenchymal stem cells, hematopoietic stem cells, pancreatic stem cells, marrow stromal stem cells, endothelial progenitor cells (EPCs), bone marrow stem cells, epidermal stem cells, hepatic stem cells, induced pluripotent cells derived from adult somatic cells, and other lineage committed adult progenitor cells.

Pluripotent stem cells, and cells derived therefrom, for use in the present methods can be obtained from any source of such cells. One means for producing pluripotent stem cells for use in the present methods is via nuclear transfer into a suitable recipient cell. Nuclear transfer using an adult differentiated cell as a nucleus donor facilitates the recovery of transfected and genetically modified stem cells as starting materials for the present methods, since adult cells are often more readily transfected than embryonic cells.

The methods may be performed with pluripotent stem cells of any animal species, including but not limited to human and non-human primate cells, ungulate cells, and rodent cells. Primate cells with which the methods may be performed include, but are not limited to, cells of humans, chimpanzees, baboons, cynomolgus monkeys, and any other New or Old World monkeys. Ungulate cells include, but are not limited to cells of bovines, porcines, ovines, caprines, equines, buffalo and bison. Rodent cells include, but are not limited to mouse, rat, guinea pig, hamster and gerbil cells.

Morphogens

As described above, morphogens, such as growth factors and chemokines, are loaded into the media at morphogen sites. Each morphogen site contains a morphogen or morphogen cocktail at a specific concentration. Through a diffusion process, a gradient of morphogen forms around the morphogen site to form a paracrine signaling area. Various paracrine signaling areas may overlap with each other leading to a mix of morphogens in the overlapped region. Over time, this diffusion gradient contacts the PS cells at the center of the device.

A variety of morphogens or morphogen combinations may be used. Morphogens include, but are not limited to decapentaplegic, Hedgehog, Sonic Hedgehog, Wingless/Wnt, epidermal growth factor, fibroblast growth factor, Insulin-like growth factor (IGF), as well as chemokines and retinoic acid. Examples of other morphogens (such as growth factors, chemokines, and cytokines) that may be tested in the disclosed assays include, but are not limited to, the Fibroblast Growth Factor family of proteins (FGF1-23), such are FGF basic and its variants, FGF acidic, the TGF beta family of proteins, including, but not limited to TGF-beta 1, TGF-beta 2, TGF-beta sRII, Latent TGF-beta, the Tumor necrosis factor (TNF) superfamily (TNFSF), including, but not limited to, TNFSF1-18, TNF-alpha, TNF-beta, the insulin-like growth factor family including but not limited to IGF-II and their binding proteins, including but not limited to, IGFBP-1, Il-1 R rp2, IGFBP-5, IGFBP-6, the matrix metalloproteinases, including but not limited to, MMP-1, CF, MMP-2, CF, MMP-2 (NSA-expressed), CF, MMP-7, MMP-8, MMP-10, MMP-9, TIMP-1, CF, TIMP-2 and other growth factors and cytokines, including but not limited to, PDGF, Flt-3 ligand, Fas Ligand, B7-1(CD80), B7-2(CD86), DR6, IL-13 R alpha, IL-15 R alpha, GRO beta/CXCL2 (aa 39-107), IL 1-18, Il-8/CXCL8, GDNF, G-CSF, GM-CSF, M-GSF, PDGF-BB, PDGF-AA, PDGF-AB, IL-2 sR alpha, IL-2 sR beta, Soluble TNF RII, IL-6 sR, Soluble gp130, PD-ECGF, IL-4 sR, beta-ECGF, TGF-alpha, TGF-beta sRII, TGF-beta 5, LAP (TGF-beta 1), BDNF, LIF sR alpha, LIF, KGF/FGF-7, Pleiotrophin, ENA-78/CXCL5, SCF, beta-NGF, CNTF, Midkine, HB-EGF, SLPI, Betacellulin, Amphiregulin, PlGF, Angiogenin, IP-10/CXCL10, NT-3, NT-4, MIP-1 alpha/CCL3, MIP-1 beta/CCL4, I-309/CCL1, GRO alpha/CXCL1, GRO beta/CXCL2, GRO gamma/CXCL3, Rantes/CCL5, MCP-1/CCL2, MCP-2/CCL8, MCP-3/CCL7, IFN-gamma, Erythropoietin, Thrombopoietin, MIF, IGF-I, IGF-II, VEGF, HGF, Oncostatin M, HRG-alpha (EGF Domain), TGF-beta 2, CNTF R alpha, Tie-2/Fc Chimera, BMP-4, BMPR-IA, Eotaxin/CCL11, VEGF R1 (Flt-1), PDGF sR alpha, HCC-1/CCL14, CTLA-4, MCP-4/CCL13, GCP-2/CXCL6, TECK/CCL25, MDC/CCL22, Activin A, Eotaxin-2/MPIF-2/CCL24, Eotaxin-3/CCL-26 (aa 24-94), TRAIL R1 (DR4), VEGF R3 (Flt-4)/SDF-1 alpha(PBSF)/CXCL12, MSP, BMP-2, HVEMNEGF R2 (KDR), Ephrin-A3, MIP-3 alpha/CCL20, MIP-3 beta/CCL19, Fractalkine/CX3CL1 (Chemokine Domain), TARC/CCL17, 6Ckine/CCL21, p75 Neurotrophin R (NGF R), SMDF, Neurturin, Leptin R/Fc Chimera, MIG/CXCL9, NAP-2/CXCL7, PARC/CCL18, Cardiotrophin-1 (CT-1), GFR alpha-2, BMP-5, IL-8/CXCL8 (Endothelial Cell Derived), Tie-1, Viral CMV UL146, VEGF-D, Angiopoietin-2, Inhibin A, TRANCE/RANK L, CD6/Fc Chimera, CF, dMIP-1 delta/LKN-1/CCL15 (68 aa), TRAIL R3/Fc Chimera, Soluble TNF RI, Activin RIA, EphA1, ENA-70, ENA-74, Eotaxin-3/CCL26, ALCAM, FGFR1 alpha (IIIc), Activin B, FGFT1 beta (Mc), LIGHT, FGFR2 beta(IIIb), DNAM-1, Follistatin, GFR alpha-3, gp 130, I-TAC/CXCL11, IFN-gamma R1, IGFBP-2, IGFBP-3, Inhibin B, Prolactin CF, RANK, FGFR2 beta (Inc), FGFR4, TrkB, GITR, MSP R, GITR Ligand, Lymphotactin/XCL1, FGFR2 alpha (Mc), Activin AB, ICAM-3 (CD50), ICAM-1 (CD54), TNF RII, L-Selectin (CD62L, BLC/BCA-1/CXCL13, HCC-4/CCL16, ICAM-2 (CD102), IGFBP-4, Osteoprotegerin (OPG), uPAR, Activin RIB, VCAM-1 (CD106), CF, BMPR-II, IL-18 R, IL-12 R beta 1, Dtk, LBP, SDF-1 alpha (PBSF)/CXCL12 (synthetic), E-Selectin (CD62E), L-Selectin (CD62L), P-Selectin (CD62P), ICAM-1 (CD54), VCAM-1 (CD106), CD31 (PECAM-1), hedgehog family of proteins, Interleukin-10, Epidermal Growth Factor, Heregulin, HER4, Heparin Binding Epidermal Growth Factor, bFGF, MIP-18, MIP-2, MCP-1, MCP-5, NGF, NGF-B, leptin, Interferon A, Interferon A/D, Interferon B, Interferon Inducible Protein-10, Insulin Like Growth Factor-II, IGB-FBP/IGF-1 Complex, C10, Cytokine Induced Neutrophil Chemoattractant 2, Cytokine Induced Neutrophil Chemoattractant 2B, Cytokine Induced Neutrophil Chemoattractant 1, Cytokine Responsive Gene-2, and any fragment thereof and their neutralizing antibodies.

Devices and Methods for Utilizing Feeder Cells

Different lineages of stem cells are needed for treating different conditions. In addition to using specific morphogens, another way to control the differentiation of stem cells is to use specific feeder cells that express various biofactors that affect stem cell differentiation. The present devices and assays allow one to screen a large number of feeder cell types or mixtures to identify those that induce proliferation, differentiation and/or chemotaxis in an optimal or desired way. Without wishing to be limited by theory, the present methods are based on the recognition that feeder cells support and eventually induce the stem cell differentiation through paracrine effects. Paracrine signaling is a form of cell signaling in which the target cell is near ("para"=near) the signal-releasing cell. Feeder cells release signal molecules (e.g., morphogen such as growth factors), which induce the differentiation of nearby stem cells.

In one aspect, the present disclosure provides methods and devices for screening different combinations of feeder cells e.g., to determine and/or optimized stem cell differentiation conditions. The methods can be used to screen different combinations of feeder cells, which may give rise to certain lineages of differentiated cells. Once the combination of feeder cells is identified, these conditions may be used on a larger scale to promote a desired stem cell differentiation.

Figure 4:
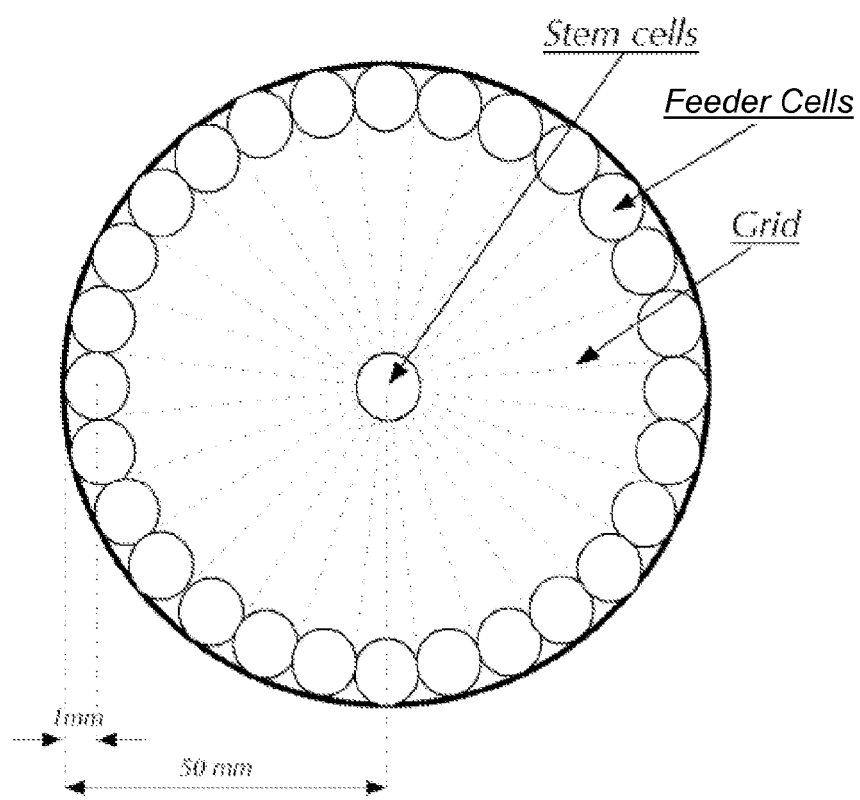
FIG. 4 is an illustrative embodiment showing one arrangement of feeder cells and stem cells on a Petri plate.
Figure 5:
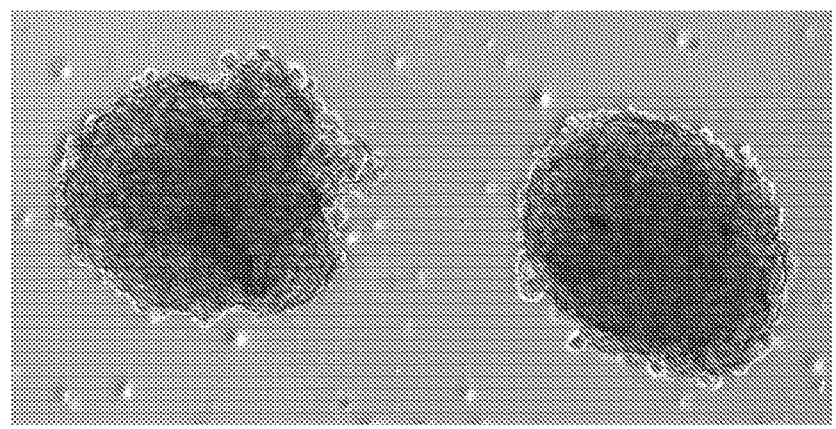
FIG. 5 is a photomicrograph showing clusters of mesenchyme stem cells (MScs) created using the hanging drop method.

The structure/configuration of devices to test feeder cells may be similar to the devices described above with regard to the morphogen assay. In one embodiment, the device comprises a round Petri dish with grids for identification of the cells once they are plated. In one embodiment, the Petri dish is coated with a layer of cell culture media. The media may include a gelatin, agarose, or agar. In some embodiments, the cells are cultured in Matrigel medium. In some embodiments, the PS cells are placed at the center of the plate. The peripheral feeder cell spots are located at the edge of the media plate surrounding the central PS cell spot. The position of each peripheral feeder cell culture site can be identified according to the grids scored to the bottom of the Petri dish. (FIG. 4). In some embodiments, the number of PS cells seeded is about 1000 cells, or about 1500 cell, or about 2000 cells. In some embodiments, the number of feeder cells seeded is about 1000 cells, or about 1500 cell, or about 2000 cells. In some embodiments, the media for the feeder cells is different from the media for the PS cells. In some embodiments, the PS cells are grown in proliferation media without differentiation factors. In some embodiments, the PS cells are grown in proliferation media with specific cell lineage directed differentiation factors.

In some embodiments, a physical barrier, such as a round tube, may be used to temporarily isolate the media having PS cells from the surrounding media allowing the PS cells to grow in the absence of any specific paracrine signaling agent. When the colony is big enough for differentiation, the physical barrier may be removed allowing the PS cells to contact the surrounding media.

In some embodiments, feeder cells are cultured at peripheral feeder cell culture sites. Each peripheral feeder cell culture site is coated with a feeder layer and wherein the feeder layer may include a single type of feeder cells or a mixture of feeder cells. Feeder cells at the peripheral feeder cell culture sites may express biofactors, e.g., signal molecules, such as, but not limited to, IGF, FGF, and TGF. The different combination of the feeder cells leads to a combination of biofactors originating from each peripheral feeder cell culture site. Through diffusion, a gradient of biofactors forms around the peripheral feeder spot to form a paracrine signaling area. Various paracrine signaling areas may overlap with each other, leading to a mix of paracrine signals in the overlapped region. The different combination of the paracrine signals, in turn, affects the stem cell differentiation. The location of the desirable lineage of cell colonies indicates a feeder cell conditions for such cell lineage. Once the conditions are identified, the conditions may be scaled-up to promote stem cell differentiation of a large number of cells of the desirable lineage.

Various feeder cells may be plated. Feeder cells include, but are not limited to, fibroblasts, such as human foreskin fibroblasts, e.g. CRL-2429 (ATCC, Manassas, USA), mouse or human derived bone marrow stromal cells (e.g. S17, RP.0.10, ST2, PA6, Ac6 or freshly isolated primary cultures), fetal liver stromal cells (e.g. FLS4.1), yolk sac cells (e.g., C166), thymic stromal cells, activated spleen cells, and endothelial cells.

Quantifying Cell Growth

In the screening assays described above, the chemotaxis or growth of cells under a particular set of conditions may also be quantified. Quantifying the growth of cells according to the present screening assays may be accomplished by a large variety of available methods, such as those that assay the amount of DNA, (e.g., the CyQuant Cell Proliferation Kit (Molecular Probes)) and then assaying the generated signal, such as fluorescence. Cell number can be quantified using agents that such as 3-(4, 5-dimethylthiazol-2-yl)-2, 5-diphenyltetrazolim bromide (MTT), 3-(4, 5-dimethylthi-azol-2-yl)-5-(3-carboxymethoxyphenyl)-2-(4-sulfophenyl)-2H-tetrazolium (MTS) [U.S. Pat. No. 5,185,450] and Ala-mar Blue which are converted to colored or fluorescent compounds in the presence of metabolically active cells. Alternatively, dyes that bind to cellular protein such as sulforhodamine B (SRB) or crystal violet can be used to quantify cell number. Alternatively, cells can be directly counted using a particle counter, such as a Coulter Counter® manufactured by Beckman Coulter, or counted using a microscope to observe cells on a hemocytometer. In one embodiment, cells counted using the hemocytometer are observed in a solution of trypan blue to distinguish viable from dead cells. Other methods of quantifying cell number are known to those of skill in the art. Other methods include labeling cells with a suitable detectable marker, such as dyes (such as Calcein AM (NeuroProbe) or the many labels available from Molecular Probes (Eugene, Oreg., U.S.A.) or radioactive labeling (e.g. cell surface iodination with $^{135}I$, protein synthesis labeling with $^{35}S$-methionine/$^{35}S$-cysteine or nucleic acid labeling).

Buffers and Cell Culture Media

Various buffers and cell culture media can be used in the devices and methods of the present technology. Any of the media may be produced as a solid or semi-solid by adding, e.g., gelatin, agarose and agar. Buffers that may be used to prepare the various solutions include cell culture media known in the art, although serum or other growth and chemotactic factors may be removed so that the results of the screening assays are not confounded and can be mostly attributable to the stem cell interaction with the morphogen or feeder cells. In some cases, a protein may be added to support the cells, such as various albumins, including bovine serum albumin. Optimal media selection depends on the cell type. Examples of suitable culture media include Iscove's Modified Dulbecco's Medium (IMDM), Dulbecco's Modified Eagle's Medium (DMEM), Minimal Essential Medium Eagle (MEM), Basal Medium Eagle (BME), Click's Medium, L-15 Medium Leibovitz, McCoy's 5A Medium, Glasgow Minimum Essential Medium (GMEM), NCTC 109 Medium, Williams' Medium E, RPMI-1640, and Medium 199. If desired, a protein-reduced or free and/or serum free medium and/or chemically defined, animal component free medium may be used, e.g., CHO, Gene Therapy Medium or QBSF Serum-free Medium (Sigma Chemical Co.; St. Louis, Mo.), DMEM Nutrient Mixture F-12 Ham, MCDB (105, 110, 131, 151, 153, 201 and 302), NCTC 135, Ultra DOMA PF or HL-1 (both from Biowhittaker; Walkersville, Md.), may be used.

If desired, the media may be further supplemented with reagents that limit acidosis of the cultures, such as buffer addition to the medium (such as N,N-bis(2-hydroxyethyl)-2-aminoethanesulfonic acid (BES), bis(2-hydroxyethyl) amino-tris(hydroxymethyl)methane (BIS-Tris), N-(2-hydroxyethyl)piperazine-N'3-propanesulfonic acid (EPPS or HEPPS), glyciclycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminom-ethane (Tris), etc.). Frequent medium changes and changes in the supplied $CO_2$ (often approximately 5%) concentration may also be used to control acidosis.

Uses of Differentiated iPS and ES Cells

The present disclosure provides differentiated PS cells produced using the methods described herein, as well as populations of such cells. The cells are capable of differentiation into many cell types and have a variety of applications and therapeutic uses. The basic properties of stem cells, i.e., the capability to infinitely self-renew and the ability to differentiate into every cell type in the body, make them ideal for therapeutic uses.

Accordingly, in one aspect the present disclosure further provides a method of treatment or prevention of a disorder and/or condition in a subject using PS cells generated from the methods described herein. The cell is cultured under suitable conditions to differentiate the cell into a desired cell type suitable for treating the condition. The differentiated cell may then be introduced into the subject to treat or prevent the condition.

The PS cells can be tailored specifically to the patient, e.g., to avoid immune rejection. Such an approach would obviate the problems associated with current transplantation methods, such as rejection of the transplanted tissue which may occur because of host versus graft or graft versus host rejection. For example, use of iPS cells in bone marrow transplants, will circumvent the requirement of providing heavy immune suppression with drugs that have potentially adverse side effects.

The PS cells may be differentiated into a number of different cell types to treat a variety of disorders by methods known in the art. For example, PS cells may be induced to differentiate into hematopoietic stem cells, muscle cells, cardiac muscle cells, liver cells, cartilage cells, epithelial cells, urinary tract cells, neuronal cells, and the like. The differentiated cells may then be transplanted back into the patient's body to prevent or treat a condition. For example, if cells of the neural lineage are desired, PS cells are changed to a culture medium containing one or more neurotrophins (such as neurotrophin 3 or brain-derived neurotrophic factor) and one or more morphogens (such as epidermal growth factor, basic fibroblast growth factor, platelet-derived growth factor, insulin-like growth factor 1, and erythropoietin). Cultured cells are optionally separated based on whether they express a marker such as A2B5 or NCAM. Neural precursors can be obtained having the capacity to generate both neuronal cells (including mature neurons), and glial cells (including astrocytes and oligodendrocytes). Additionally or alternatively, replicative neuronal precursors can be obtained that have the capacity to form differentiated cell populations in which at least 5% of all the cells in the population express tyrosine hydroxylase, a marker of dopaminergic neurons. If cells of the hepatocyte lineage are desired, then PS cells may be cultured in the presence of a histone deacetylase inhibitor such as n-butyrate. The cultured cells are optionally cultured simultaneously or sequentially with a hepatocyte maturation factor, such as EGF, insulin, and FGF. If cells expressing characteristic markers of cardiomyocytes are desired, differentiation is facilitated by nucleotide analogs that affect DNA methylation (such as 5-aza-deoxy-cytidine), growth factors, and bone morphogenic proteins. The cells can be further enriched by density-based cell separation, and maintained in media containing creatine, carnitine, and taurine.

The methods can also be used in the treatment or prevention of neurological diseases. Such diseases include, for example, Alzheimer's disease, Parkinson's disease, Huntington's disease, amyotrophic lateral sclerosis (ALS), lysosomal storage diseases, multiple sclerosis, spinal cord injuries and the like.

The cells produced in the methods can be utilized for repairing or regenerating a tissue or differentiated cell lineage in a subject. The method includes obtaining a differentiated cell as described herein and administering the cell to a subject (e.g., a subject having a myocardial infarction, congestive heart failure, stroke, ischemia, peripheral vascular disease, alcoholic liver disease, cirrhosis, Parkinson's disease, Alzheimer's disease, diabetes, cancer, arthritis, wound healing, immunodeficiency, aplastic anemia, anemia, and genetic disorders) and similar diseases, where an increase or replacement of a particular cell type/tissue or cellular de-differentiation is desirable. In one embodiment, the subject has damage to the tissue or organ, and the administering provides a dose of cells sufficient to increase a biological function of the tissue or organ or to increase the number of cell present in the tissue or organ. In another embodiment, the subject has a disease, disorder, or condition, and wherein the administering provides a dose of cells sufficient to ameliorate or stabilize the disease, disorder, or condition. In yet another embodiment, the subject has a deficiency of a particular cell type, such as a circulating blood cell type and wherein the administering restores such circulating blood cells.

Differentiated cells can also be used for tissue reconstitution or regeneration in a human patient in need thereof. The cells are administered in a manner that permits them to graft to the intended tissue site and reconstitute or regenerate the functionally deficient area.

For purposes of commercial distribution, cells are typically supplied in the form of a pharmaceutical composition comprising an isotonic excipient, and prepared under conditions that are sufficiently sterile for human administration. For general principles in medicinal formulation of cell compositions, see *Cell Therapy: Stem Cell Transplantation, Gene Therapy, and Cellular Immunotherapy*, by G. Morstyn & W. Sheridan eds, Cambridge University Press, 1996; and Hematopoietic Stem Cell Therapy, E. D. Ball, J. Lister & P. Law, Churchill Livingstone, 2000. The cells may be packaged in a device or container suitable for distribution or clinical use, optionally accompanied by information relating to use of the cells in tissue regeneration, or restoring a therapeutically important metabolic function.

Kits

Components to carry out the screening assays described may be assembled into kits, containers, packs, or dispensers together with instructions. When supplied as a kit, the different components of the devices may be packaged in separate containers and admixed immediately before use. Such packaging of the components separately may permit long-term storage without losing the active components' functions. For example, a kit may include a Petri dish, cell culture media, and one or more morphogens or feeder cells.

The reagents included in the kits can be supplied in containers of any sort such that the life of the different components are preserved, and are not adsorbed or altered by the materials of the container. For example, sealed glass ampules may contain lyophilized chemokine or a buffer that has been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix; for example, lyophilized morphogen in one compartment, and a buffer or water in the other. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

EXAMPLES

Example 1—Formation of Mesenchymal Stem Cell Clusters

To observe stem cell migration, human mesenchymal stem cells (MSCs) derived from bone marrow were examined for their ability to cluster in suspension and then migrate away from the cluster once cultured on a device of the present technology.

A. Materials and Methods

To create CXCR4-expressing mesenchymal stem cells (MSCs), a lentivirus construct was used to transduce human bone marrow-derived MSCs. Induced mesenchymal stem cells (iMSCs) were generated from either cord blood (CB)- or adult peripheral blood (PB)-CD34(+) cells by direct reprogramming with a single factor, OCT4. In the presence of a GSK3 inhibitor, 16% of the OCT4-transduced CD34(+) cells were converted into iMSCs within 2 weeks. Direct reprogramming was achieved with both episomal vector-mediated transient OCT4 expression and lentiviral vector-mediated OCT4 transduction. The iMSCs express MSC markers, resemble bone marrow (BM)-MSCs in morphology, and possess in vitro multi-lineage differentiation capacity. FACS analysis, using phycoerythrin labeled anti-CXCR4 antibody (BioLegend) was performed to test for CXCR4 expression. Briefly, cells were stained for cell surface marker CXCR4 by incubation with the antibody for 30 minutes at room temperature. Flow cytometric analysis was performed using FACS Aria II (BD Biosciences, San Jose, Calif.) with a 488-nm laser. Thirty thousand events were collected for each sample.

B. Formation of Stem Cell Clusters

About $1\times10^4$ CXCR4 expressing MSCs were suspended in 20 μl-50 μl of medium. The MSC media was composed of knockout DMEM/F12 medium (Invitrogen) supplemented with 20% knockout serum replacement (Invitrogen), 1 mmol/l GlutaMAX (Invitrogen), 2 mmol/l nonessential amino acids (Invitrogen), 1×penicillin/streptomycin (Invitrogen), 0.1 mmol/l β-mercaptoethanol (Sigma-Aldrich, St Louis, Mo.), 20 ng/ml FGF2 (ProSpec). Next, 20 μl-50 μl of medium and cells were pipetted onto a coverslip. The coverslip was then covered by a slide containing a ring of paraffin wax to create a small space around the cell droplet. The coverslip and slide were then quickly inverted, creating a "hanging drop" for culturing. Cells were cultured for about 4 hours at 37° C. prior to seeding on the device for migration assays.

FACS analysis, as described above, was performed to determine CXCR4 expression in the cell clusters after the 4 hour incubation. Results indicate that about 20% of mixed cells from clumps by hanging drop assay expressed CXCR4 on their surface.

Example 2—Polarized Cell Migration of MSCs with Morphogen Exposure

Clusters of MSC, formed as described in Example 1, were examined for their ability to migrate directionally upon exposure to a morphogen gradient.

A. Preparing the Cell Migration Matrix

One embodiment of a screening device of the present technology that mimics the extracellular matrix was made as follows. High grade agarose (Ultrapure, Sigma) was dissolved in culture medium at a concentration between 0.3% and 0.6% in 2×DMEM/F12 medium and FBS, melted and poured into a 35 mm cell culture dish at the maximum thickness of 2 mm (in this embodiment, about 1 ml was poured into the 35 mm cell culture dish). After the agarose gel was completely solidified, two wells established by punching the agarose using a cloning cylinder (Sigma). One well was placed in the center of the dish and the second well was placed on the edge of the dish. The wells were about 6 mm apart, with each well about 1-2 mm in diameter and about 2 mm in depth. About 0.5 ml of Matrigel® was then poured as a thin layer across the entire surface of the agarose, including filling the two wells.

B. Establishing SDF-1 Expressing "Feeder Cells"

To create a morphogen gradient using SDF-1, fibroblasts "feeder cells" were transfected to express SDF-1 as follows. Human SDF-1 cDNAs were purchased from Open Biosystems (Huntsville, Ala.) and cloned into the pRRLSin.cPPT.PGK-GFP.WPRE lentiviral vector (Addgene, Cambridge, Mass., Plasmid 12252) by PCR cloning. The constructs were verified by sequencing. For lentivirus production, a standard calcium phosphate precipitation protocol was used. Titers of $5-10\times10^7$/ml were routinely achieved after a 100-fold concentration by centrifugation at 6,000 g for 24 hours at 4° C. A mitomycin C-inactivated CF-1 fibroblast cells (Applied Stemcell, Menlo Park, Calif.) were seeded into 24-well plates at $1\times10^4$ cell/well that were precoated with RetroNectin (CH-296; Takara Bio, Shiga, Japan) for lentiviral transduction for 4-5 hours. A second transduction was conducted 24 hours later. One day after transduction, the fibroblasts were harvested and transferred to 6-well plates. The SDF-1 expressing fibroblasts were maintained in the MSC media condition for 2 more days before being used as the source of mitogen C. Seeding Stem Cells and Feeder Cells on the Device for Migration Testing Cell clusters were formed from CXCR4-expressing MSCs using the hanging drop method as described in Example 1. MSCs ($1\times10^4$) were cultured in drops between 20 μl and 50 μl for about 4 hours. Culture clumps were harvested and incubated in 20-50 μl liquid media for 4-8 hours, and then mixed with the matrigel before seeding into the center well. After 3-5 days, the migration of MSCs were observed.

About 1000 SDF-1-expressing fibroblasts (feeder cells) were also seeded into the outer well. Controls were run by seeding CXCR4 expressing MSCs cells in the center wells of the device. In a first control, the outer well remained empty; no SDF-1-expressing fibroblasts were seeded into this well. In second control, the second well of the device was seeded with fibroblasts that do not express SDF-1 (non-transfected fibroblast feeder cells).

Cells were incubated at 37° C. at 5% $CO_2$ (i.e., standard cell culture conditions).

D. Results

Figure 6A:
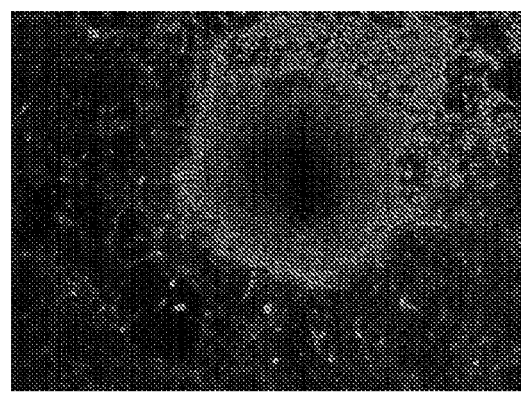
FIGS. 6A and 6B are photomicrographs of mesenchyme stem cell (MSC) clusters cultured for 3 days (FIG. 6A) and 5 days (FIG. 6B) in a device containing a well containing feeder cells that express SD-1.
Figure 6B:
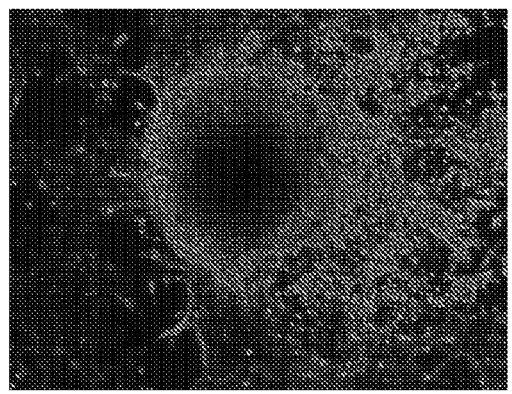

After 5 days of incubation, CXCR4 expressing mesenchymal stem cell clusters in the control devices exhibited little to no migration. CXCR4 expressing mesenchymal stem cell clusters seeded in a device including SDF-1 expressing fibroblasts in the outer well began showing a polarized migration pattern beginning at about 3 days in culture. MSC migration away from the seed clusters showed a distinct polarization towards the outer well of the device (i.e., toward the SGF-1 fibroblast containing well). FIG. 6A shows the polarized morphology of cell migration in an MSC cluster cultured for 3 days. FIG. 6B shows the polarized morphology of cell migration in another MSC cluster cultured for 5 days in the device.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference in their entireties and for all purposes to the same extent as if each individual publication, patent, or patent application was specifically and individually incorporated by reference in its entirety for all purposes.

What is claimed is:

1. A method for identifying a pluripotency profile of stem cells comprising:
   culturing one or more stem cells in a cell culturing system, wherein the cell culturing system comprises a cell culturing plate comprising a layer of cell culturing substrate, a cell culture site comprising the one or more stem cells, and one or more morphogen sites comprising one or more morphogens, wherein the one or more morphogen sites are each positioned peripheral to the cell culture site, and wherein each of the one or more morphogen sites are separated by physical barriers in the cell culturing plate;
   incubating the cell culturing system under conditions suitable to allow the one or more stem cells to differentiate into one or more differentiated cells and migrate on the cell culturing plate in response to the one or more morphogens; and
   determining the migration pattern of the one or more differentiated cells on the cell culturing plate, wherein the migration pattern of the one or more differentiated cells is indicative of the pluripotency profile of the population of stem cells.

2. The method of claim 1, further comprising isolating the one or more differentiated cells that have migrated towards the one or more morphogen sites.

3. The method of claim 1, wherein the migration of a desired differentiated cell on the cell culturing plate towards the one or more morphogen sites is indicative of a target morphogen condition to induce differentiation.

4. The method of claim 1, wherein the migration of the one or more differentiated cells towards a morphogen site is indicative of a stem cell morphogen present in the morphogen site.

5. The method of claim 1, wherein the one or more morphogen sites comprise different concentrations of the same morphogen.

6. The method of claim 1, wherein each of the one or more morphogen sites comprise a different morphogen.

7. The method of claim 1, wherein the cell culture site is surrounded by a physical barrier.

8. The method of claim 7, wherein the physical barrier is removed from around the cell culture site.

9. The method of claim 1, wherein each of the one or more morphogen sites are an equal distance away from the cell culture site.

10. The method of claim 1, wherein each of the one or more morphogen sites comprise a chemokine or growth factor.

11. The method of claim 10, wherein the chemokine or growth factor comprises a molecule selected from the group consisting of: decapentaplegic (Dpp), transforming growth factor beta (TGF-β), hedgehog, sonic hedgehog, wingless/wnt, epidermal growth factor, fibroblastic growth factor, insulin-like growth factor, retinoic acid, and mixtures thereof.

12. The method of claim 1, wherein the cell culturing plate is physically divided into one or more compartments.

13. A method for identifying a pluripotency profile of stem cells comprising:
    culturing one or more stem cells in a cell culturing system, wherein the cell culturing system comprises a cell culturing plate comprising a layer of cell culturing substrate, a cell culture site comprising the one or more stem cells, and one or more morphogen sites comprising one or more feeder cells, wherein the one or more morphogen sites are each positioned peripheral to the cell culture site;
    incubating the cell culturing system under conditions suitable for the feeder cells to produce one or more morphogens, and to allow the one or more stem cells to differentiate into one or more differentiated cells and migrate on the cell culturing plate; and
    determining the migration pattern of the one or more differentiated cells on the cell culturing plate, wherein the migration pattern of the one or more differentiated cells is indicative of the pluripotency profile of the population of stem cells.

14. The method of claim 13, further comprising isolating the one or more differentiated cells that have migrated towards the one or more morphogen sites.

15. The method of claim 13, wherein the migration of a desired differentiated cell on the cell culturing plate towards the one or more morphogen sites is indicative of a feeder cell population for desirable stem cell differentiation.

16. The method of claim 13, wherein the migration of the one or more differentiated cells towards the one or more feeder cells in the morphogen site is indicative of a feeder cell type useful to induce differentiation of the stem cell.

17. The method of claim 13, wherein the one or more feeder cells comprise a heterogeneous population of feeder cells or a homogenous population of feeder cells.

18. The method of claim 13, wherein each of the one or more morphogen sites are separated by physical barriers in the cell culturing plate.

19. The method of claim 13, wherein the cell culture site is surrounded by a physical barrier.

20. The method of claim 19, wherein the physical barrier is removed from around the cell culture site.

21. The method of claim 13, wherein each of the one or more morphogen sites are an equal distance away from the cell culture site.

22. The method of claim 13, wherein each of the one or more morphogen sites physically overlap one another.

23. The method of claim 13, wherein the one or more feeder cells secrete a chemokine or growth factor.

24. The method of claim 23, wherein the chemokine or growth factor comprises a molecule selected from the group consisting of: decapentaplegic (Dpp), transforming growth factor beta (TGF-β), hedgehog, sonic hedgehog, wingless/wnt, epidermal growth factor, fibroblastic growth factor, insulin-like growth factor, retinoic acid, and mixtures thereof.

25. The method of claim 13 wherein the cell culturing plate is visually or physically divided into one or more compartments.

26. A method for identifying a feeder a cell population for stem cell differentiation comprising:
culturing one or more stem cells in a cell culturing system, wherein the cell culturing system comprises a cell culturing plate comprising a layer of cell culturing substrate, a cell culture site comprising the one or more stem cells, and one or more morphogen sites comprising one or more test feeder cells, wherein the one or more morphogen sites are each positioned peripheral to the cell culture site;
incubating the cell culturing system under conditions suitable for the feeder cells to produce one or more morphogens, and to allow the one or more stem cells to differentiate into one or more differentiated cells and migrate on the cell culturing plate; and
determining the migration pattern of the one or more differentiated cells on the cell culturing plate, wherein the migration pattern of the one or more differentiated cells is indicative of efficacy of test feeder cells on stem cell differentiation.

27. The method of claim 26, wherein the migration of a desired differentiated cell on the cell culturing plate towards the one or more morphogen sites is indicative of a feeder cell population for desirable stem cell differentiation.

28. The method of claim 26, wherein the migration of the one or more differentiated cells towards the one or more feeder cells in the morphogen site is indicative of a feeder cell type useful to induce differentiation of the stem cell.

29. A method for identifying a stem cell morphogen comprising:
culturing one or more stem cells in a cell culturing system, wherein the cell culturing system comprises a cell culturing plate comprising a layer of cell culturing substrate, a cell culture site comprising the one or more stem cells, and two or more morphogen sites comprising one or more test agents, wherein each of the two or more morphogen sites is positioned peripheral to the cell culture site, and wherein each of the two or more morphogen sites physically overlap one another;
incubating the cell culturing system under conditions suitable to allow the one or more stem cells to differentiate into one or more differentiated cells and migrate on the cell culturing plate in response to the one or more test agents; and
determining the migration pattern of the one or more differentiated cells on the cell culturing plate, wherein the migration pattern of the one or more differentiated cells is indicative of test agents' efficacy as a morphogen.

30. The method of claim 29, wherein the migration of a desired differentiated cell on the cell culturing plate towards the two or more morphogen sites is indicative of a target morphogen condition to induce differentiation.

31. The method of claim 29, wherein the migration of the one or more differentiated cells towards a morphogen site is indicative of a stem cell morphogen present at said site.

32. A cell culturing system comprising a cell culturing plate, wherein the cell culturing plate comprises a layer of cell culturing substrate; a cell culture site comprising one or more stem cells; and two or more morphogen sites, wherein each of the two or more morphogen sites is positioned peripheral to the cell culture site, and wherein each of the two or more morphogen sites physically overlap one another.

33. The cell culturing system of claim 32, wherein the two or more morphogen sites comprise different concentrations of the same morphogen.

34. The cell culturing system of claim 32, wherein each of the two or more morphogen sites comprise a different morphogen.

35. The cell culturing system of claim 32, wherein the two or more morphogen sites comprise one or more feeder cells.

36. The cell culturing system of claim 35, wherein the two or more morphogen sites comprise a heterogeneous population of feeder cells or a homogeneous population of feeder cells.

37. The cell culturing system of claim 32, wherein the cell culture site is surrounded by a physical barrier.

38. The cell culturing system of claim 37, wherein the physical barrier is removed from around the cell culture site.

39. The cell culturing system of claim 32, wherein each of the two or more morphogen sites are an equal distance away from the cell culture site.

40. The cell culturing system of claim 32, wherein each of the two or more morphogen sites comprise a chemokine or growth factor.

41. The cell culturing system of claim 40, wherein the chemokine or growth factor comprises a molecule selected from the group consisting of: decapentaplegic (Dpp), transforming growth factor beta (TGF-β), hedgehog, sonic hedgehog, wingless/wnt, epidermal growth factor, fibroblastic growth factor, insulin-like growth factor, retinoic acid, and mixtures thereof.

42. The cell culturing system of claim 32, wherein the cell culturing substrate comprises an ingredient selected from the group consisting of gelatin, agarose and agar.

43. The cell culturing system of claim 42, wherein the cell culturing substrate is solid or semi-solid.

44. The cell culturing system of claim 32, wherein the cell culturing plate is visually or physically divided into one or more compartments.

* * * * *